US006410872B2

(12) United States Patent
Campbell et al.

(10) Patent No.: US 6,410,872 B2
(45) Date of Patent: *Jun. 25, 2002

(54) AGRICULTURAL ARTICLE INSPECTION APPARATUS AND METHOD EMPLOYING SPECTRAL MANIPULATION TO ENHANCE DETECTION CONTRAST RATIO

(75) Inventors: Duncan B. Campbell, Central Point, OR (US); James Ewan, Los Altos, CA (US); Cliff J. Leidecker, Rogue River, OR (US); H. Parks Squyres; Hooshmand M. Kalayeh, both of Medford, OR (US)

(73) Assignee: Key Technology, Inc., Walla Walla, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/461,079

(22) Filed: Dec. 14, 1999

Related U.S. Application Data

(63) Continuation-in-part of application No. 09/277,568, filed on Mar. 26, 1999, now Pat. No. 6,225,620.

(51) Int. Cl.[7] .............................................. B07C 5/342
(52) U.S. Cl. ...................... 209/577; 209/576; 209/580; 209/587; 209/938
(58) Field of Search ................................ 209/576, 577, 209/580, 581, 582, 587, 938; 250/339.11, 340, 341.8, 349, 350; 356/407, 448, 237.1

(56) References Cited

U.S. PATENT DOCUMENTS

| | | | | |
|---|---|---|---|---|
| 3,758,824 A | * | 9/1973 | Warneke ..................... 315/246 |
| 4,146,135 A | * | 3/1979 | Sarkar et al. ................ 209/580 |
| 4,186,836 A | * | 2/1980 | Wassmer et al. ............ 209/565 |
| 4,515,275 A | * | 5/1985 | Mills et al. .................. 209/558 |
| 4,535,470 A | * | 8/1985 | Mills ........................... 209/588 |
| 5,077,477 A | * | 12/1991 | Stroman et al. ............. 250/349 |
| 5,315,384 A | | 5/1994 | Heffington et al. ............ 348/93 |
| 5,440,127 A | | 8/1995 | Squyres .................... 250/341.8 |
| 5,464,981 A | | 11/1995 | Squyres et al. ........... 250/341.8 |
| 5,659,624 A | * | 8/1997 | Fazzari et al. ............... 382/110 |
| 5,791,497 A | * | 8/1998 | Campbell et al. ............ 209/577 |
| 5,808,305 A | | 9/1998 | Leidecker et al. ........ 250/341.8 |
| 5,960,098 A | * | 9/1999 | Tao ............................. 382/110 |
| 5,984,366 A | * | 11/1999 | Priddy .......................... 283/72 |
| 6,080,950 A | * | 6/2000 | Jalink .......................... 209/577 |
| 6,252,188 B1 | * | 6/2001 | Zapata et al. ................ 209/577 |

* cited by examiner

*Primary Examiner*—Donald P. Walsh
*Assistant Examiner*—Joseph Rodriguez
(74) *Attorney, Agent, or Firm*—Wells St. John P.S.

(57) ABSTRACT

A sorting system (110) conveys articles, such as peaches (114) on a conveyor belt (112) past an inspection zone (126) that is lighted by an illumination source (90) radiating a number of emission peaks over visible and infrared portions of the spectrum. The illumination source generates the radiation from an Indium Iodide lamp (92) that is reflected off a parabolic reflector (94) and through a "soda straw" collimator (100) to illuminated the peaches. A detector system (118) employs line scanning visible and infrared cameras (142, 140) to sense visible and IR wavelength reflectance values for the peach meat (124) and peach pit or pit fragments (126). Various image processing and analysis methologies, such as subtraction, ratio, logarithmic, regression, combination, angle, distance, and shape may be employed to enhance the image contrast and classify the resulting data for sorting the peaches. Employing subtraction also cancels "glint" caused by specular reflections of the illumination source off the peaches and into the cameras.

13 Claims, 13 Drawing Sheets

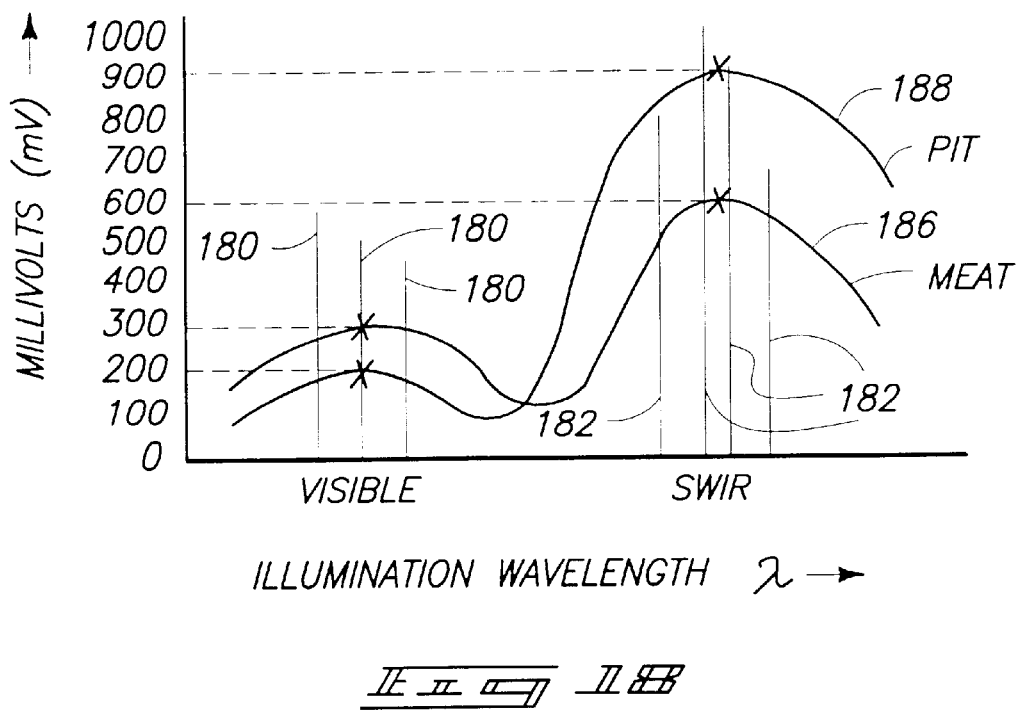
_Fig. 18_
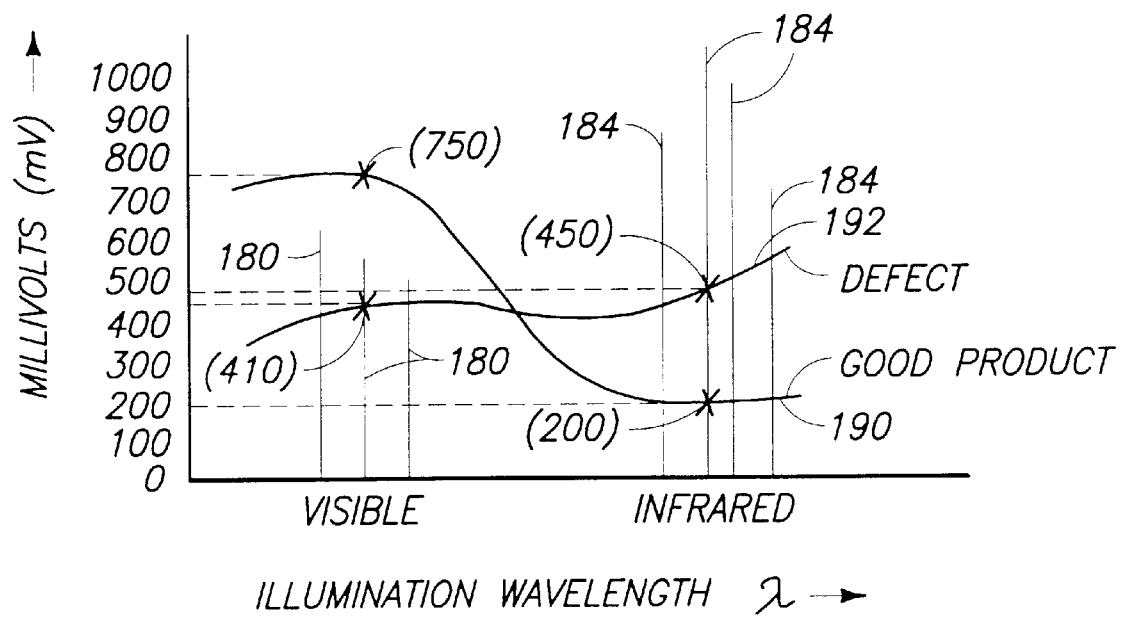
_Fig. 19_

AGRICULTURAL ARTICLE INSPECTION APPARATUS AND METHOD EMPLOYING SPECTRAL MANIPULATION TO ENHANCE DETECTION CONTRAST RATIO

RELATED APPLICATIONS

This patent application is a continuation-in-part application of U.S. patent application Ser. No. 09/277,568 filed Mar. 26, 1999, entitled "Peach Pit Detection Apparatus and Method", naming Duncan B. Campbell, James Ewan, Cliff J. Leidecker and H. Parks Squyres as inventors, now U.S. Pat. No. 6,225,620 which issued May 1, 2001.

TECHNICAL FIELD

This invention relates to agricultural product inspection and more particularly to an apparatus and a method of inspecting peach halves for pits and pit fragments.

BACKGROUND OF THE INVENTION

A popular agricultural product is canned peach halves, slices and cubes. The peach variety typically used for canning is referred to as a "cling" peach, whereas the popular eating peach variety is referred to as "the free stone" peach, which is not used for canning because they lose their taste during the canning process. The variety names cling and free stone imply the relative ease with which the stone (hereafter "pit") can be removed from the fruit.

Many peach processors employ an Atlas splitting machine to remove the pit. This machine consist of a circumferential knife, that looks and functions much like the iris of a camera lens. As the blades of the machine close down on the peach, it cuts through the flesh until it meets the hard core of the pit. Once the pit is secured firmly in place by means of the blade, two cups approach from either side to grab the two peach halves. When the cups are in place they are rotated in opposite directions to twist the peach halves apart and separate them from the secured pit. Unfortunately, the blade cannot always adequately secure the pit and when the peach halves fall away, the entire pit may stay embedded in one of the halves. Alternatively, the pit may split in half or fragment into smaller pieces.

Successful removal of pits from cling peaches presents a considerable agricultural processing challenge. In conventional agricultural processing plants, split peach halves are visually inspected for pits or pit fragments by large numbers of inspectors standing on opposite sides of conveyors belts used to transport the peach halves. Unfortunately, the pit color closely matches the color of peach flesh. This is due in part to tendrils of peach flesh that cling to the surface of the pit. Therefore, the inspectors must rely on their visual shape recognition capabilities to recognize unacceptable product. Moreover, the inspectors often have to manually detect small "hidden" pit fragments by wiping the tip of their fingers around the cavity left in the peach by a removed pit. These inspection difficulties have previously ruled out automatically inspecting peach halves with machine vision techniques that detect visual wavelengths of light because the close color match between peach flesh and pits and the hidden nature of many pit fragments would render such inspection unreliable.

Improving machine vision inspection reliability involves careful attention to the camera or cameras employed, the illumination of the product being inspected, and the image processing methodologies. Suitable illumination typically employs a uniform, shadowless, high intensity light source to illuminate the product being inspected. Prior light sources include fluorescent lamps, incandescent bulbs, and short and long arc discharge lamps. The assignee of this application, SRC Vision, of Medford, Oreg. has used all of these sources and found them wanting in one aspect or another.

For example, FIG. 1 shows a "Brite-Lite" illumination source 10 manufactured by the assignee of this application, in which a fluorescent tube 12 is mounted at one foci of an elliptical or parabolic reflector 14 and the other foci lies in a linear inspection zone 16 on the plane of a conveyor belt 18 moving articles 20 to be inspected. A line scanning inspection camera 22 has its field of view that is co-aligned with the energy from fluorescent tube 12 focused in inspection zone 16 to maximize the amount of illumination reflected off articles 20 and received by inspection camera 22. This illumination technique produces a fairly uniform illumination inspection zone 16, but the illumination decreases near the edges of belt 18 because light illuminating the center of belt 18 propagates from any and all points along the length of fluorescent tube 12. However, because fluorescent tube 12 has a finite length and extends only five or six inches beyond the belt edges, illumination reaching points near the belt edges propagates mainly from portions of fluorescent tube 12 directly over the belt and, to a lesser extent, from any short portions that extend beyond the belt edges. Moreover, this technique is not entirely shadowless, which makes pit fragment detection difficult. Consider an article with some height, such as an apple cube lying within inspection zone 16. A point lying immediately to one side of the cube will receive light from only that portion of fluorescent tube 12 that extends in a direction away from that side of the cube. The cube itself will block the light from that portion of fluorescent tube 12 that extends in the direction of the cube. There is, however, some partial filling in of the shadow by that portion of fluorescent tube 12 that is not blocked by the cube.

To provide shadowless illumination, the light rays should ideally be parallel and perpendicular to the surface of belt 18. One way to produce this ideal illumination is to employ an illumination point source at an infinite distance. However, this technique is impractical because the illumination intensity decreases inversely with the square of the distance from the light source.

FIG. 2 shows another exemplary illumination source 30 that employs multiple incandescent lamps 32 each having an associated reflector. Illumination source 30 simulates multiple illumination point sources propagating from a significant distance, but is not very energy efficient because the illumination from each of lamps 32 is spread over a relatively large area of belt 18. Illumination uniformity is approximated by appropriately aiming lamps 32 and by adjusting their individual illumination levels. This is a labor intensive process that is prone to errors. Moreover, indiscriminate adjustment of lamp 32 illumination levels may alter their spectral wavelength distributions.

FIG. 3 shows yet another exemplary illumination source 40 that employs a pair of moderate length high-intensity discharge ("HID") tubes 42 positioned at the foci of two astigmatic cylindrical projection lenses 44. In illumination source 40, only those light rays that intersect flat back surfaces 46 of projection lenses 44 are focused on inspection zone 16 of conveyor belt 18, which renders this technique inefficient. Moreover, because the lengths of HID tubes 44 is short compared to the width of belt 18, the light rays must diverge to spread across the width of belt 18, which introduces shadows because the angle of incidence of the light rays is not perpendicular to belt 18. Using multiple HID lamps 44 and projection lenses 44 can somewhat alleviate this problem.

What is needed, therefore, is an illumination and detection technique and image processing methodology that is suitable for automatically inspecting peach halves, slices, and dices for pits and pit fragments.

OBJECTS OF THE INVENTION

An object of this invention is, therefore to overcome the shortcomings of the prior art.

Another object of this invention is to provide an automated electro-optical means for detecting faulty articles in a low contrast and low signal level environment.

A further object of this invention is to provide for the automated detection of peach pits and pit fragments in peach flesh.

Yet another object of this invention is to provide an illumination source, a detector, and an image analysis method suitable for achieving the objects of this invention.

In the context of this invention, contrast C is defined as follows:

$$C = \frac{R_\lambda^{PIT}}{R_\lambda^{FLESH}} \text{ or } \frac{S^{PIT}}{S^{FLESH}}$$

where R=Reflectivity and S=Signal (Intensity). S is further defined as:

$$S = \int_{\lambda_1}^{\lambda_2} R(\lambda)L(\lambda)C(\lambda)F(\lambda)d\lambda$$

where $R(\lambda)$=the spectral reflectivity of an article; $L(\lambda)$=the spectral emission of an illumination source; $C(\lambda)$=the spectral response of a camera; and $F(\lambda)$=the spectral response of a filter.

A sorting system of this invention conveys agricultural articles, such as peach halves, some of which include pits or pit fragments, on a conveyor belt past an inspection zone that is lighted by an illumination source that radiates both visible and infrared ("IR") radiation. The illumination source generates numerous peaks of visible and IR radiation over a broad spectrum. A preferred illumination source includes a high-pressure Indium Iodide doped high intensity discharge lamp. The radiation is reflected off a parabolic reflector and through a "soda straw" collimator to illuminated the peaches. A detector system employs line scanning visible and IR cameras to sense visible and IR wavelength reflectance value differences existing between the peach meat and the peach pit or pit fragments. Because peach flesh and peach pits exhibit a reversal in the reflectance values between the visible and IR wavelengths, an image analysis technique, such as subtraction or division, is employed to enhance the image contrast. The data subtraction technique also cancels "glint" caused by specular reflections of the illumination off the peaches and into the cameras. In other embodiments of this invention, the visible and infrared image data may be processed using various other image processing methods, such as ratioing, logarithmic, regression, combination, statistical distance, and shape determination to enhance the image detection contrast and classify the resulting data to make sorting decisions.

Additional objects and advantages of this invention will be apparent from the following detailed description of preferred embodiments thereof that proceed with reference to the accompanying drawings.

BRIEF DESCRIPTION OF THE DRAWINGS

FIGS. 18 and 19 are graphical representations of reflectance versus illumination wavelength of two agricultural product examples.

DETAILED DESCRIPTION OF PREFERRED EMBODIMENTS

Figure 4:
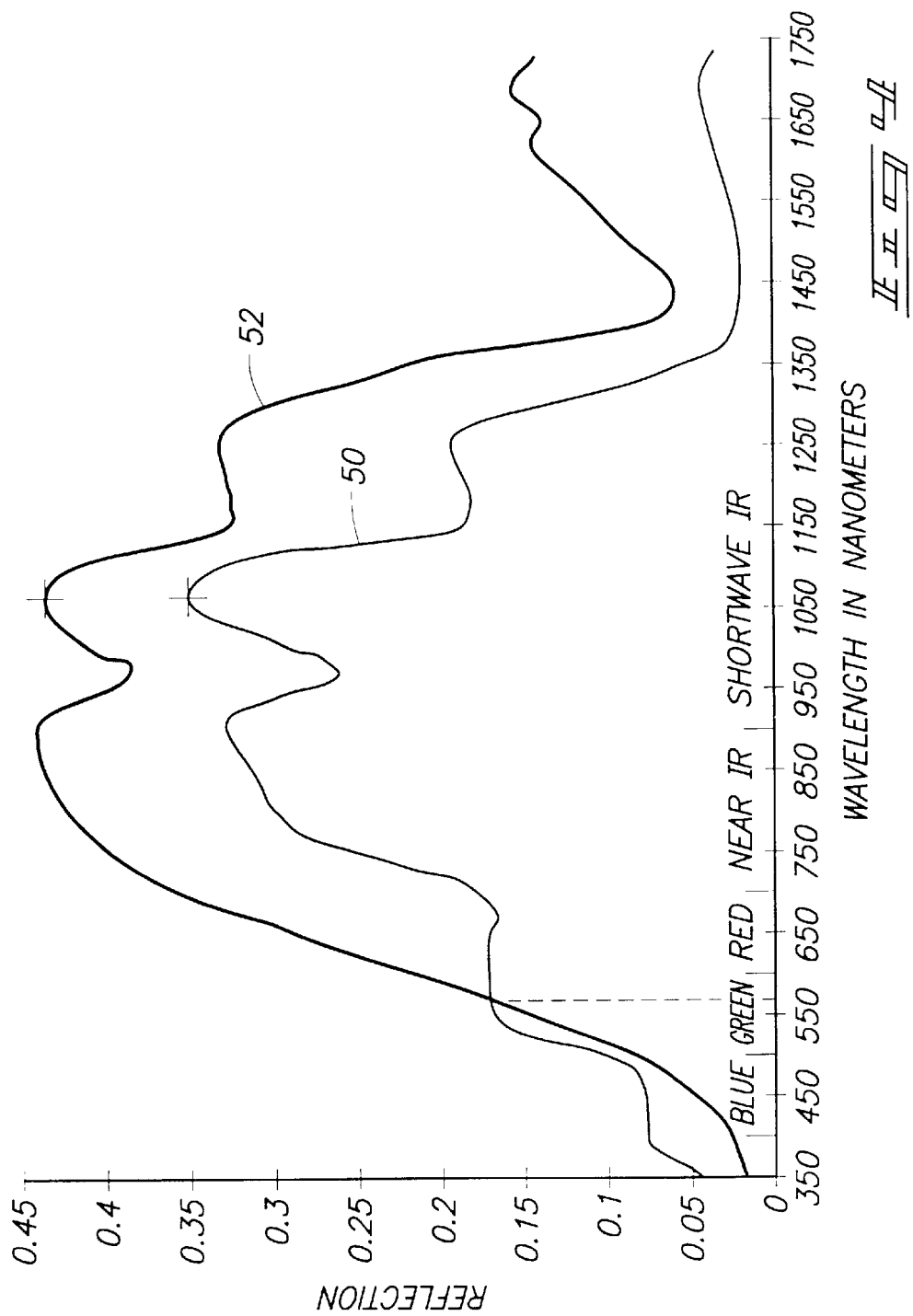
FIG. 4 is a graphical representation of the reflectance versus illumination wavelength of Chilean Cling peach flesh and peach pits.

The inventors have discovered that there is a reversal of reflectivity between peach meat and peach pits in the visible versus the IR portions of the electromagnetic spectrum, at which wavelengths peach pits reflect significantly more energy than peach flesh. For example, FIG. 4 shows spectro-radiographic scans representing the reflectance of Chilean Cling peach flesh 50 and peach pits 52 taken at visible and IR wavelengths ranging from 350 nanometers ("nm") to 1750 nm. Chilean peach meat 50 exhibits more reflectance in the blue visible wavelengths between 400 nm and 560 nm than does Chilean peach pits 52. However, the reflectance of flesh 50 and pits 52 reverses at about 560 nm and diverges rapidly in the IR wavelengths above 700 nm.

Figure 5:
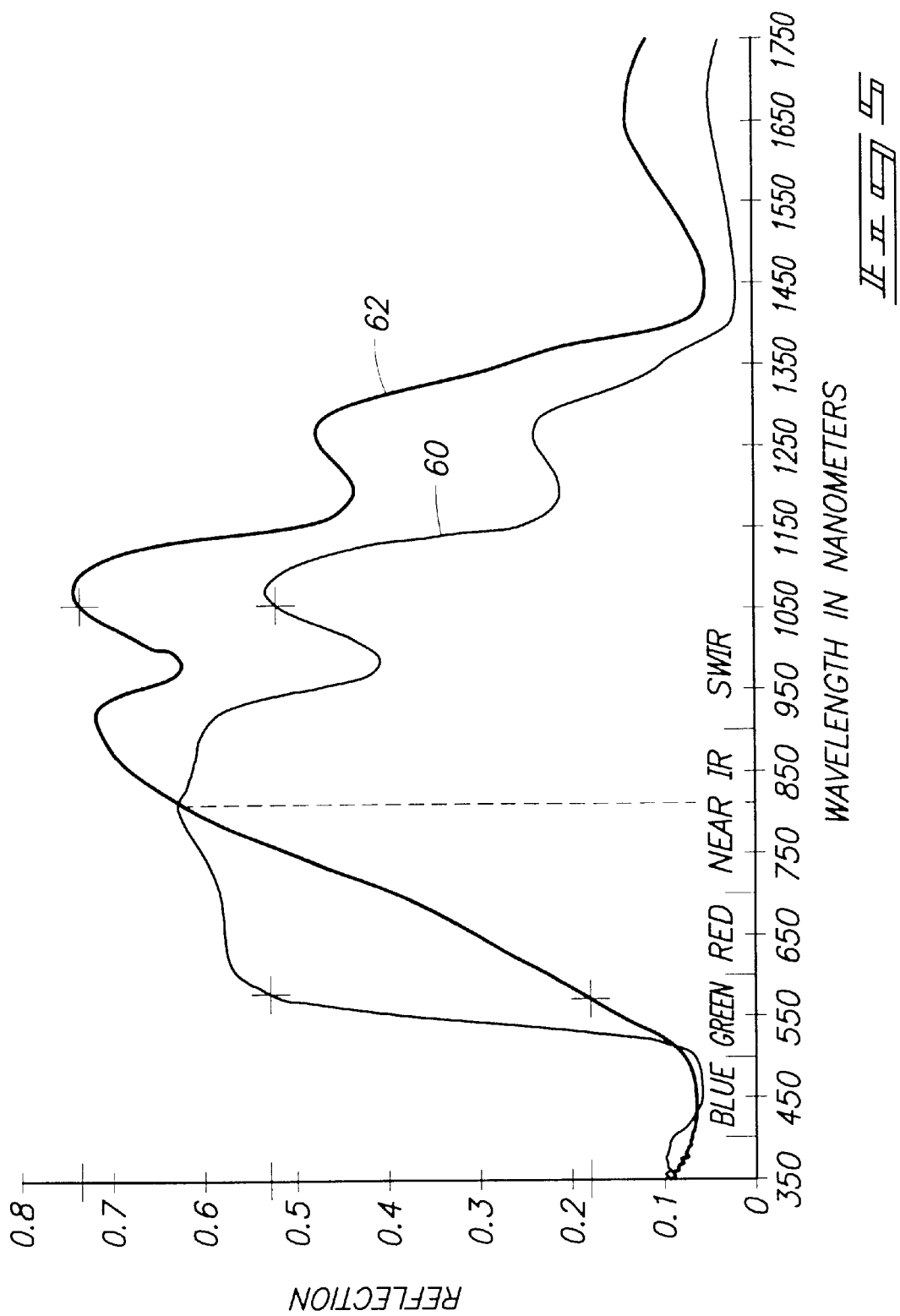
FIG. 5 is a graphical representation of the reflectance versus illumination wavelength of Australian peach flesh and peach pits.

In another example, FIG. 5 shows spectro-radiographic scans representing the reflectance of Australian peach flesh 60 and peach pits 62 taken at visible and IR wavelengths ranging from 350 nm to 1750 nm. Australian peach meat 60 exhibits more reflectance in the green and red visible wavelengths between 510 nm and 700 nm than does Australian peach pits 62. However, the reflectance of flesh 60 and pits 62 reverses and diverges rapidly in the IR wavelengths above 800 nm.

To exploit these reflectance differences, this invention illuminates the peach halves with a source of electromagnetic energy rich in the energy wavelengths of interest and detects the reflected visible and IR energy with a camera or cameras that are sensitive to those wavelengths.

There are numerous illumination sources that emit energy in the visible and/or IR portions of the electromagnetic spectrum including incandescent sources, such as hot wires. However, most of these sources emit their energy over an excessively broad portion of the spectrum and are, therefore, inefficient and insufficiently concentrated in the desired portion of the spectrum to cause reflections to be successfully detected by a line scanning camera. A suitable illumination source should efficiently and brightly emit all or most of its energy at the desired wavelength or wavelength ranges depending on the articles and defects being inspected. Alternatively, multiple illumination sources having different spectral emissions can be used to produce illumination having selected spectral bands for detecting and classifying particular articles and defects. Of course, lowpass, highpass, and bandpass filters can be added to tune and select particular illumination spectra of interest.

Figure 6:
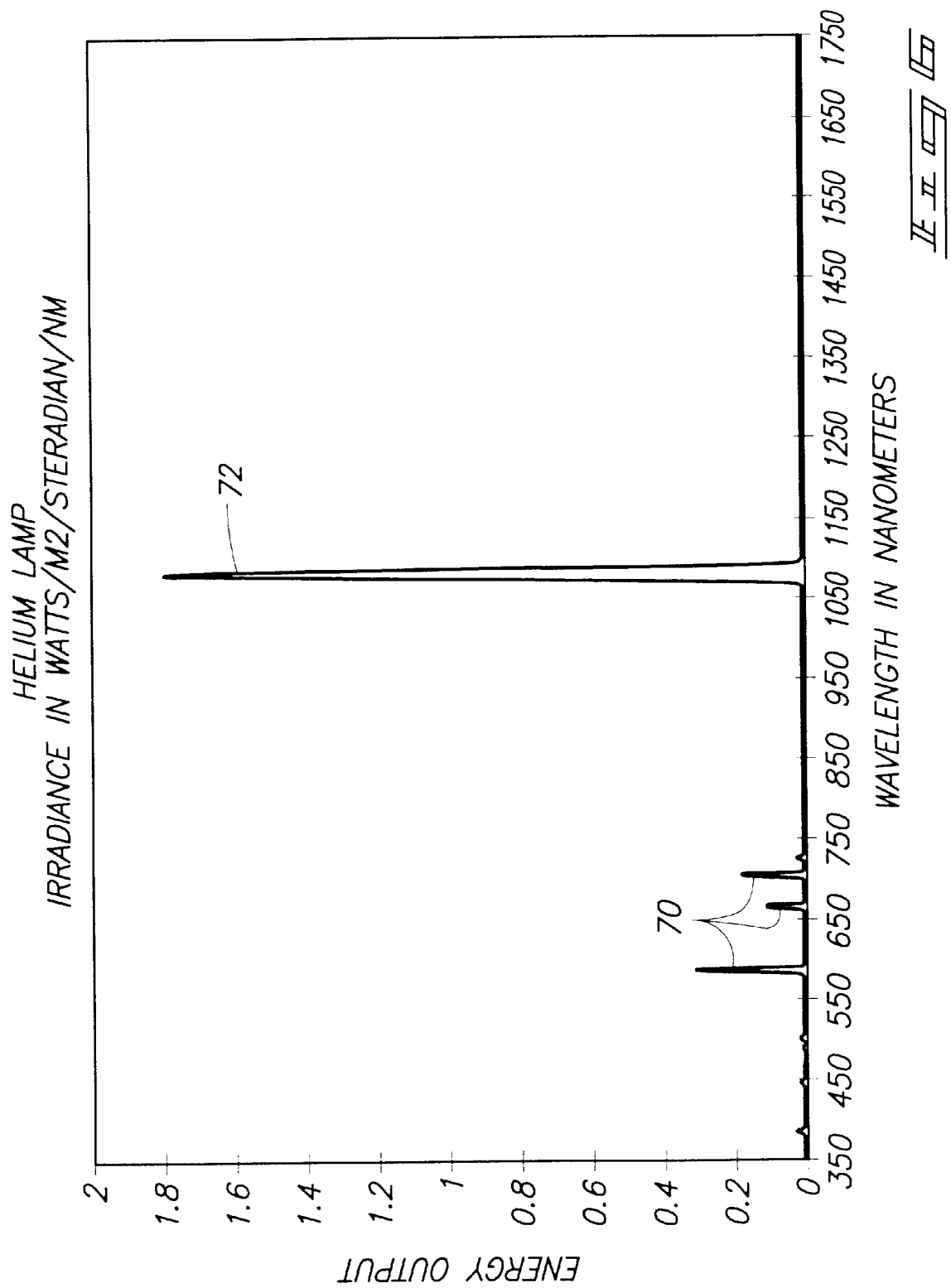
FIG. 6 is a graphical representation of the energy output versus wavelength of a Helium plasma discharge illumination source.
Figure 7:
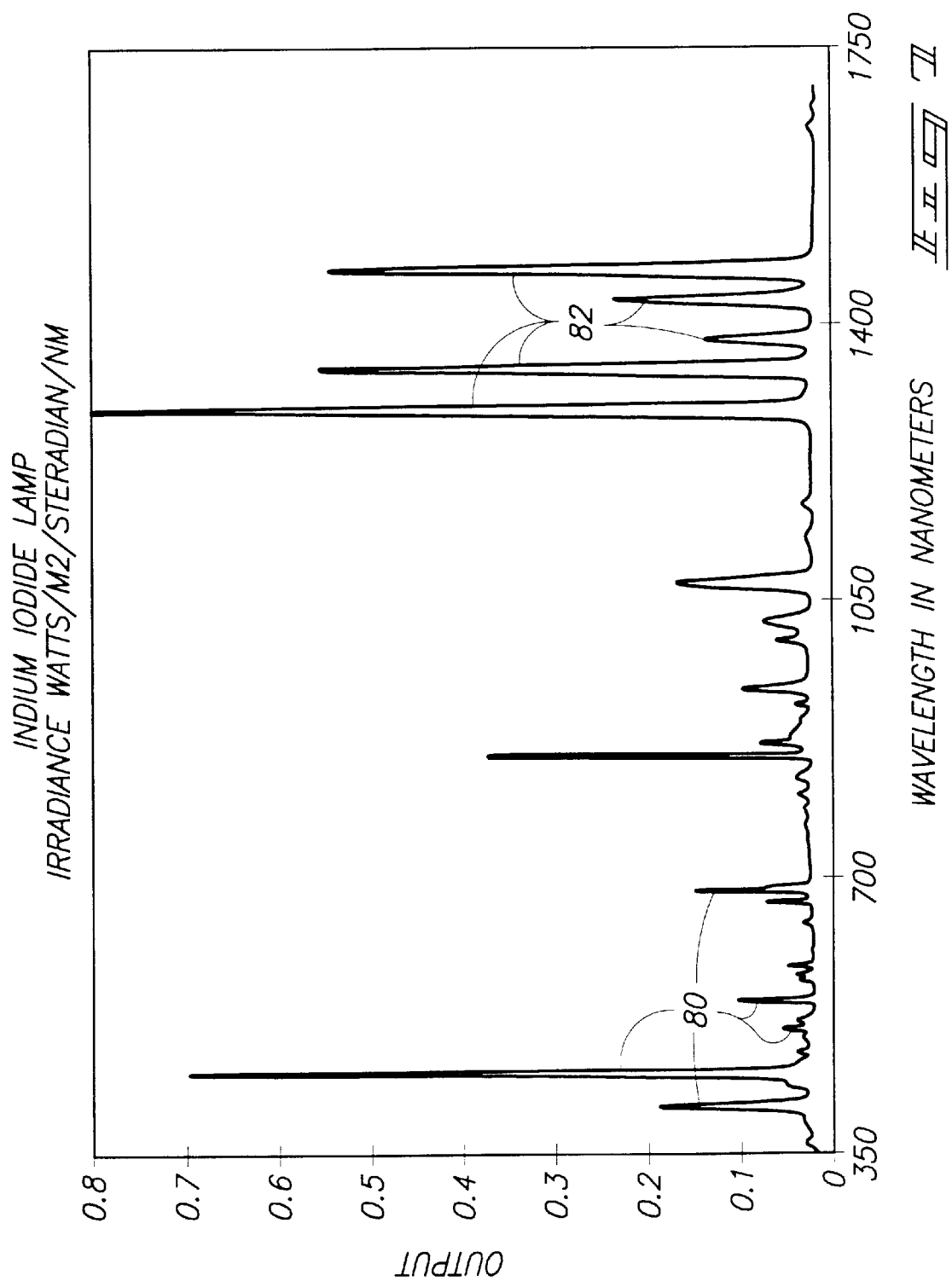
FIG. 7 is a graphical representation of the energy output versus wavelength of an Indium Iodine arc discharge illumination source.

FIGS. 6 and 7 show the spectral energy distributions of two suitable illumination sources for inspecting peaches.

In particular, FIG. 6 shows the energy output spectrum of a Helium gas filled lamp that is manufactured by the assignee of this application. The spectrum includes visible wavelength energy lines 70 and a high energy IR line 72 at about 1,080 nm, which is a suitable wavelength for detection of Chilean or Australian peach pits or fragments of peach pits.

Likewise, FIG. 7 shows the energy output spectrum of an Indium Iodide arc discharge lamp that is manufactured by Specialty Discharge Lighting, located in Bellevue, Ohio. The spectrum includes energy in four major visible wavelength lines 80 ranging from 411 nm to 690 nm and five major IR energy lines ranging from 1,280 nm to 1,470 nm, which are preferred wavelength ranges for detecting reflectance differences between peach meats, peach pits, and pit fragments.

In machine vision-based inspection systems, reliable detection depends on achieving suitable contrast and signal-to-noise ratios. The contrast may be described as the ratio of defect (pit or fragment) reflectivity to good product (peach meat) reflectivity at a predetermined wavelength or wavelengths. As shown in FIG. 4, the contrast of Chilean peach pits to peach flesh at 1,080 nm (Helium lamp) is about 0.43:0.34, or about 1.26:1. For the Indium Iodide illumination source, the contrast is a weighted average of the contrasts computed for each of the major lines. The weighting factor for each line is proportional to the fractional portion of the overall energy in each given line. For the five lines 82 between 1,280 nm and 1,470 nm, the first line's weighting factor is about 20 percent of the total. For the first line the contrast is about 0.34:0.18, or 1.89:1.

The contrast at 1,080 nm (Helium lamp) of the Australian peach pit 62 to meat 60 is approximately 0.72/0.53=1.38:1, whereas at 580 nm in the visible portion of the spectrum, the contrast of pit 62 to meat 60 is 0.18/0.52=0.34:1.

Clearly, the visible and IR contrasts are more detectable with the Indium Iodide source than with the Helium source.

The Signal to Noise ratio may be described as the ratio of signal energy (reflected light received by the camera and converted into an electronic signal) generated by the camera to the stochastic (time varying) noise energy (snow) generated by the camera. If the desired peach and pit images are obscured by snow, distinguishing between them is difficult no matter how high the contrast. The amount of signal energy depends on the spectral energy of the light illumination source, the reflectivity of the object being inspected, the F-number of the camera lens, the "exposure time" of the camera, the spectral response of the camera, and the spectral response of any filter(s) that are in the path of the illumination or the reflected image energy. In this invention, the Indium Iodide source provides significantly more signal energy than the Helium lamp. Even though the reflectivity of the product and defect is higher at 1080 nm, the relatively low intensity of the Helium source renders the Indium Iodide source as the preferred illumination source.

The camera stochastic noise level depends on noise generated by hole/electron pairs recombining within the photodetector array chosen and is proportional to the absolute temperature and the square root of the signal processing bandwidth. In this invention, an Indium Gallium Arsenide ("InGaAs") photodetector array is preferred because its sensitivity peaks between 1,000 nm and 1,600 nm. Suitable InGaAs photodetector arrays are available from Sensors Unlimited, Inc. of Princeton, N.J. Fortunately, in this wavelength range the quantum efficiency of the InGaAs photodetector array is very high (approaching 80 percent) and the noise is relatively low. A figure of merit that expresses the ratio of photodetector sensitivity to stochastic noise generation is referred to as Noise Equivalent Power, which is the amount of signal needed to equal the noise generated by the photodetector. For InGaAs photo detectors, the measured Noise Equivalent Power is about $5.12 \times 10^{-13}$ watts. This very low noise power means that the amount of signal energy received by the photodetector can be correspondingly low and still maintain a usable signal to noise ratio. This confirms that the Helium illumination source is a viable alternative to the Indium Iodide illumination source.

Figure 8:
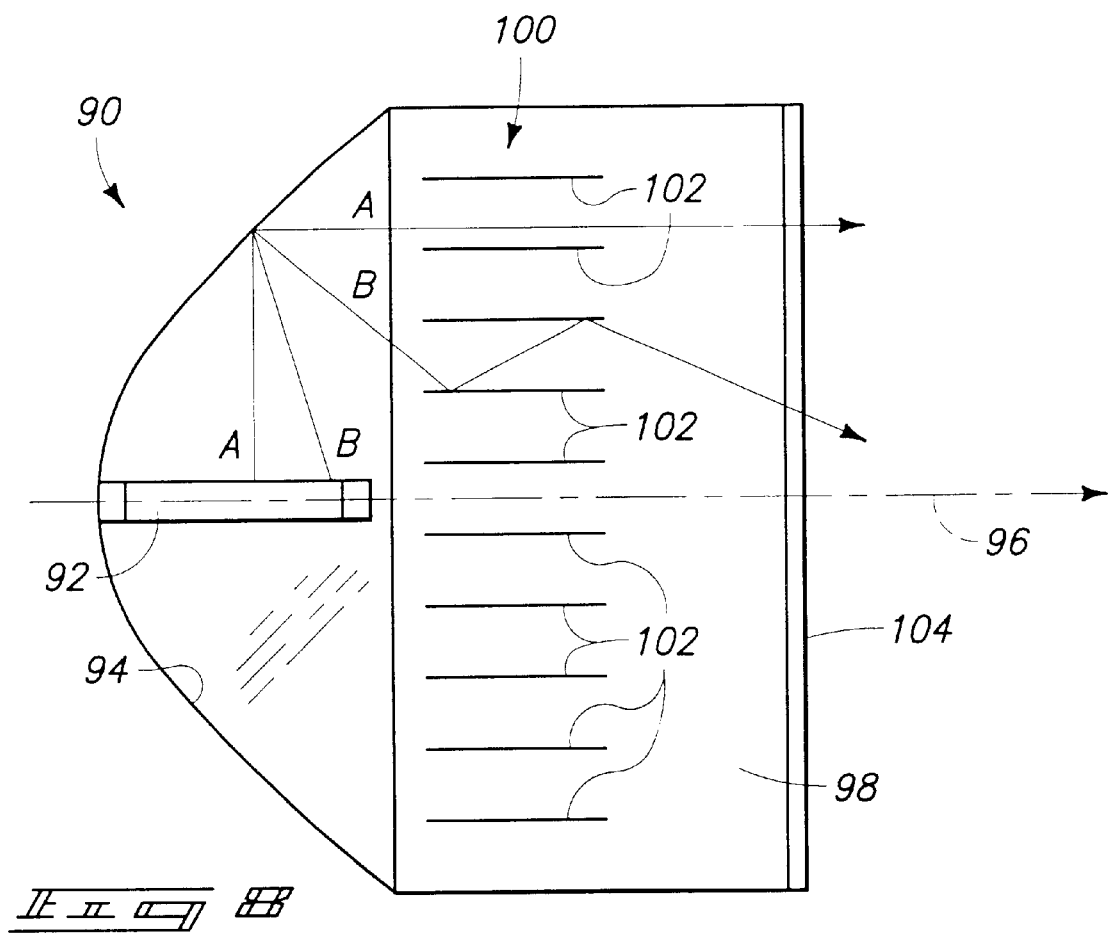
FIGS. 8 and 9 are plan and elevation views of a preferred Indium Iodine illumination source of this invention showing a parabolic reflector, parallel mirror surfaces, and a "soda straw collimator.
Figure 9:
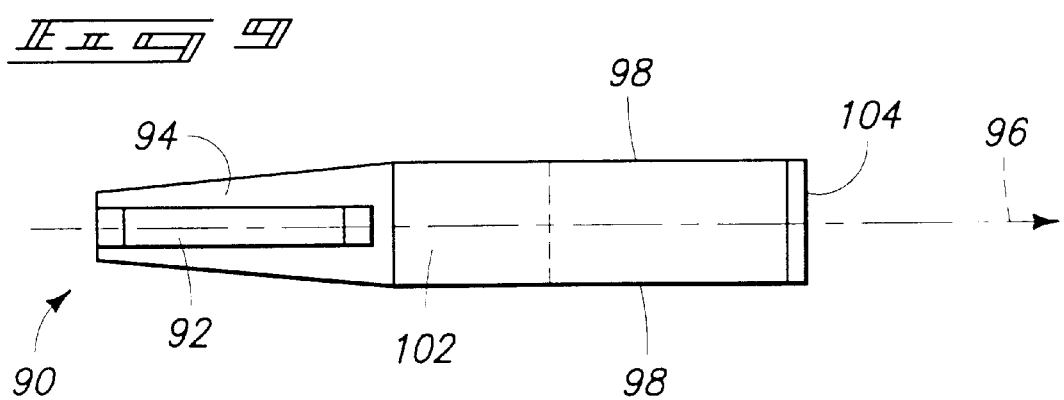

FIGS. 8 and 9 show plan and elevation views of a preferred illumination source 90 of this invention that provides uniform, intense, parallel illumination of a linear inspection zone. An HID lamp 92, having a length of about 30 cm (12 inches) and filled with a Indium Iodine gas mixture, is positioned at the focus of a cylindrical parabolic reflector 94. HID lamp 92 is oriented so that its longitudinal axis is aligned with a projection axis 96 of reflector 94. Reflector 94 is formed from polished aluminum having a protective dielectric surface coating and may be gold-plated to enhance its IR reflectivity. Illumination source 90 includes mirror-surfaced top and bottom caps 98 that are angled outwardly from lamp 92 and become parallel planar mirror surfaces after emerging from reflector 94. Top and bottom caps 98 may also be gold-plated to enhance their IR reflectivity. Substantially all the light rays propagating from HID lamp 92 are received by reflector 94 and caps 98 and are reflected generally along projection axis 96.

A "soda straw collimator" 100 comprises multiple walls 102 extending perpendicularly between top and bottom caps 98 and aligned parallel to projection axis 96. Walls 102 have diffuse surfaces and their length to pitch ratio allows only light rays that are substantially parallel to projection axis 96 to exit illumination source 90, thereby virtually eliminating any shadowing that would be detrimental to detecting peach pits or pit fragments.

In particular, consider light rays A and B, which propagate along typical paths. Light ray A emanates from the center of HID lamp 92 and reflects off reflector 94 in a direction substantially parallel to projection axis 96. However, light ray B emanates from an end of HID lamp 92 and reflects off reflector 94 in a direction that is not parallel to projection axis 96. Soda straw collimator 100 diffuses and/or absorbs all light rays B that strike walls 102 at high incident angles and passes all light rays B that strike walls 102 at zero, low, or glancing, angles of incidence.

The exit aperture of illumination source 90 may be covered with an optional protective window 104 formed from a material transmissive to visible and IR radiation.

Figure 10:
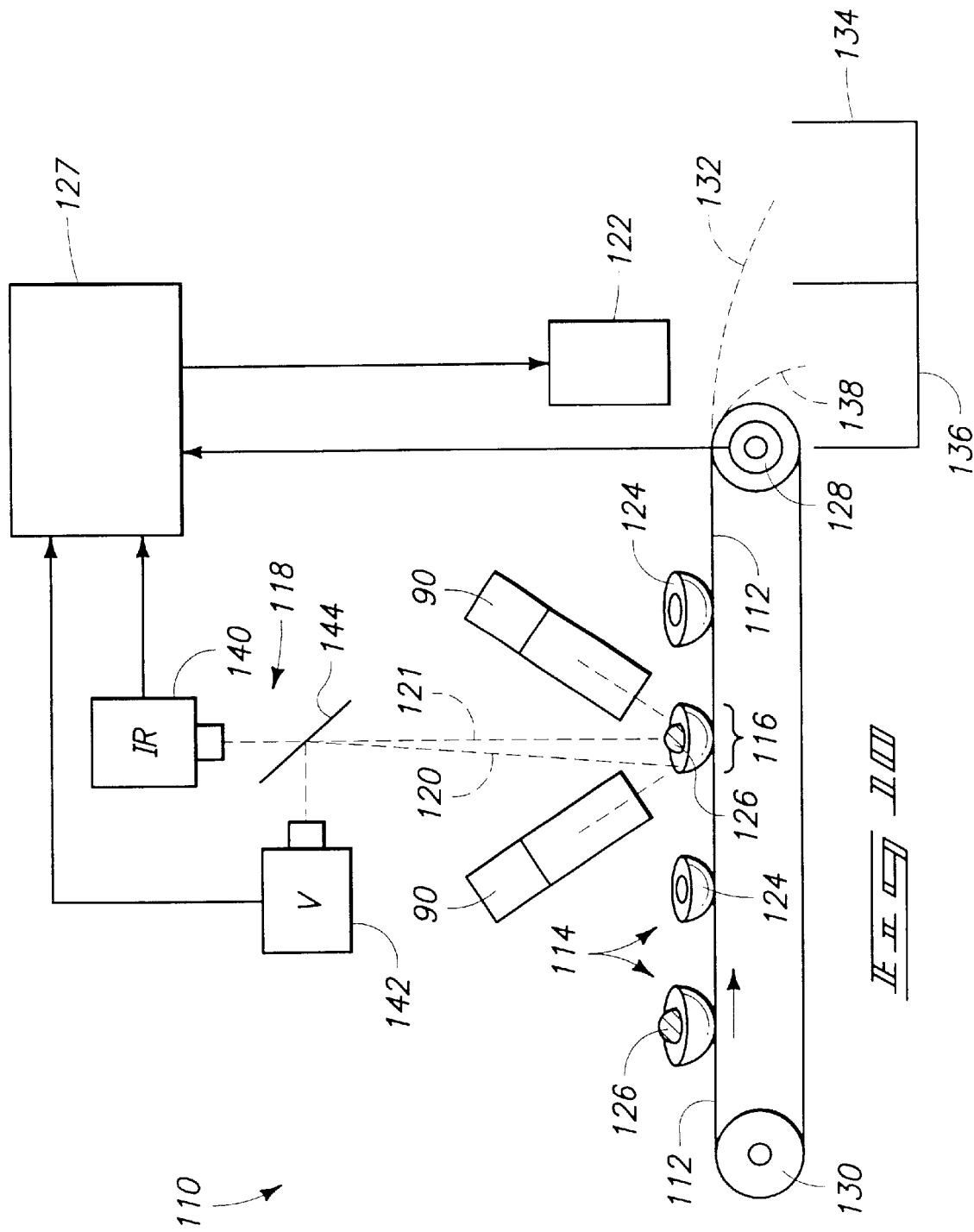
FIG. 10 is a schematic pictorial view of a peach sorting system of this invention.

FIG. 10 shows a peach sorting system 110 constructed in accordance with this invention. Generally, the system 110 includes: an endless conveyor belt 112 for transporting peaches 114 through an inspection zone 116; at least one, but preferably two of illumination sources 90 for illuminating peaches 114 in inspection zone 116; a detector system 118 for detecting reflected rays 120 and 121; a sorting system 122 for sorting peach pit and pit fragments 126 from peach meat 124; and a control system 126 for controlling the operation of sorting system 122 based on signals from detector system 118 and a rotary shaft encoder 128 coupled to conveyor belt 112. Although peaches 114 are inspected on conveyor belt 112 in the illustrated embodiment, it will be appreciated that in-the-air (e.g., off belt) inspection or other techniques may be employed if desired.

Endless conveyor belt 112 is driven by a motorized drive roller 130 at a speed selected so that acceptable peaches 114 are projected from conveyor belt 112 along a trajectory 132 into an accept area 134, unless deflected by sorting system 122 into a reject area 136 along a trajectory 138. Preferably, conveyor belt 112 is provided with a black matte or other anti-reflective surface finish to reduce background reflections and improve the effective signal-to-noise ratio detected by detector system 118. Peaches 114 may be singulated or distributed in an essentially random fashion across the length and width of conveyor belt 112.

Figure 1:
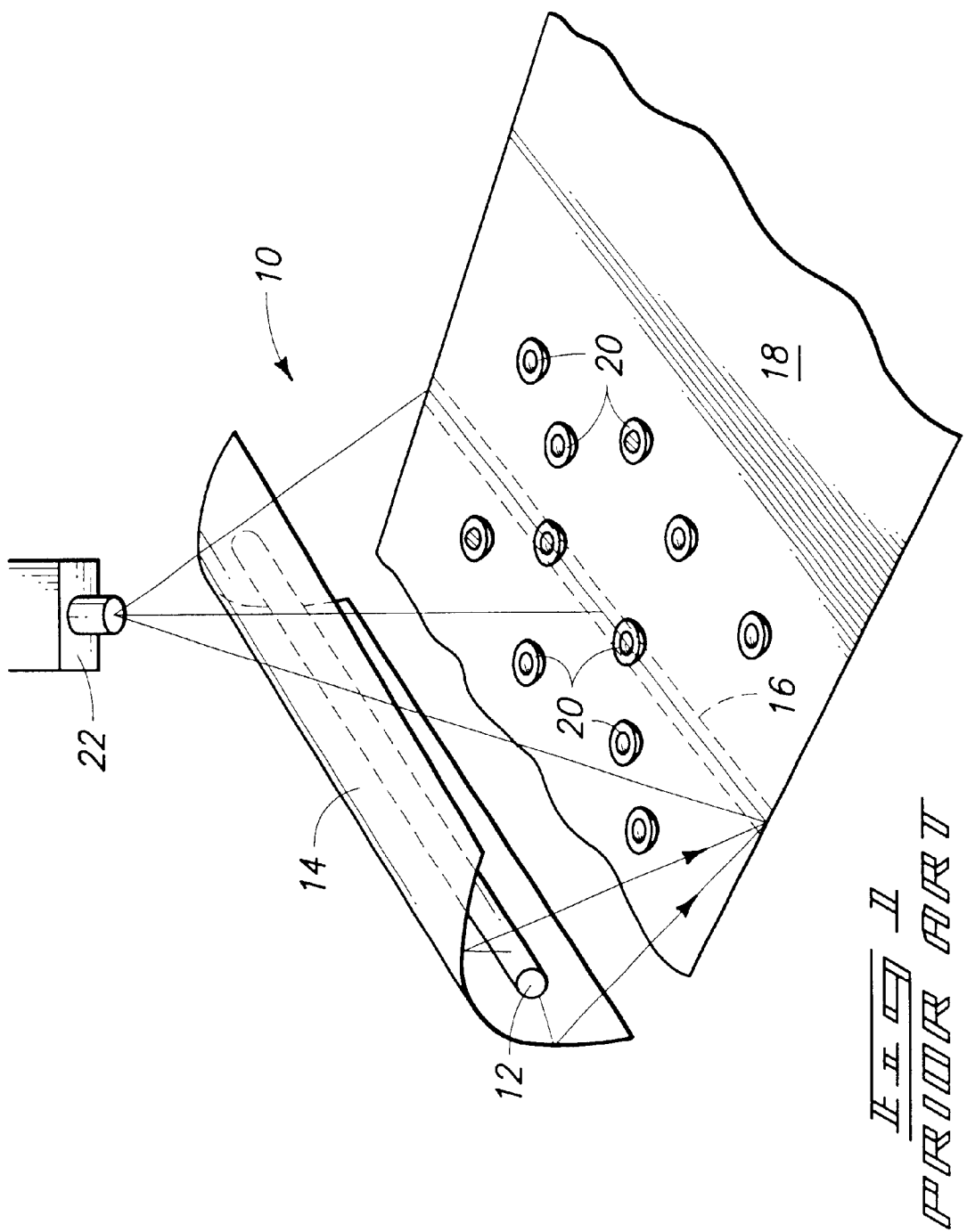
FIG. 1 is an isometric pictorial view of a prior art illumination source showing a fluorescent tube mounted at one foci of a reflector.
Figure 2:
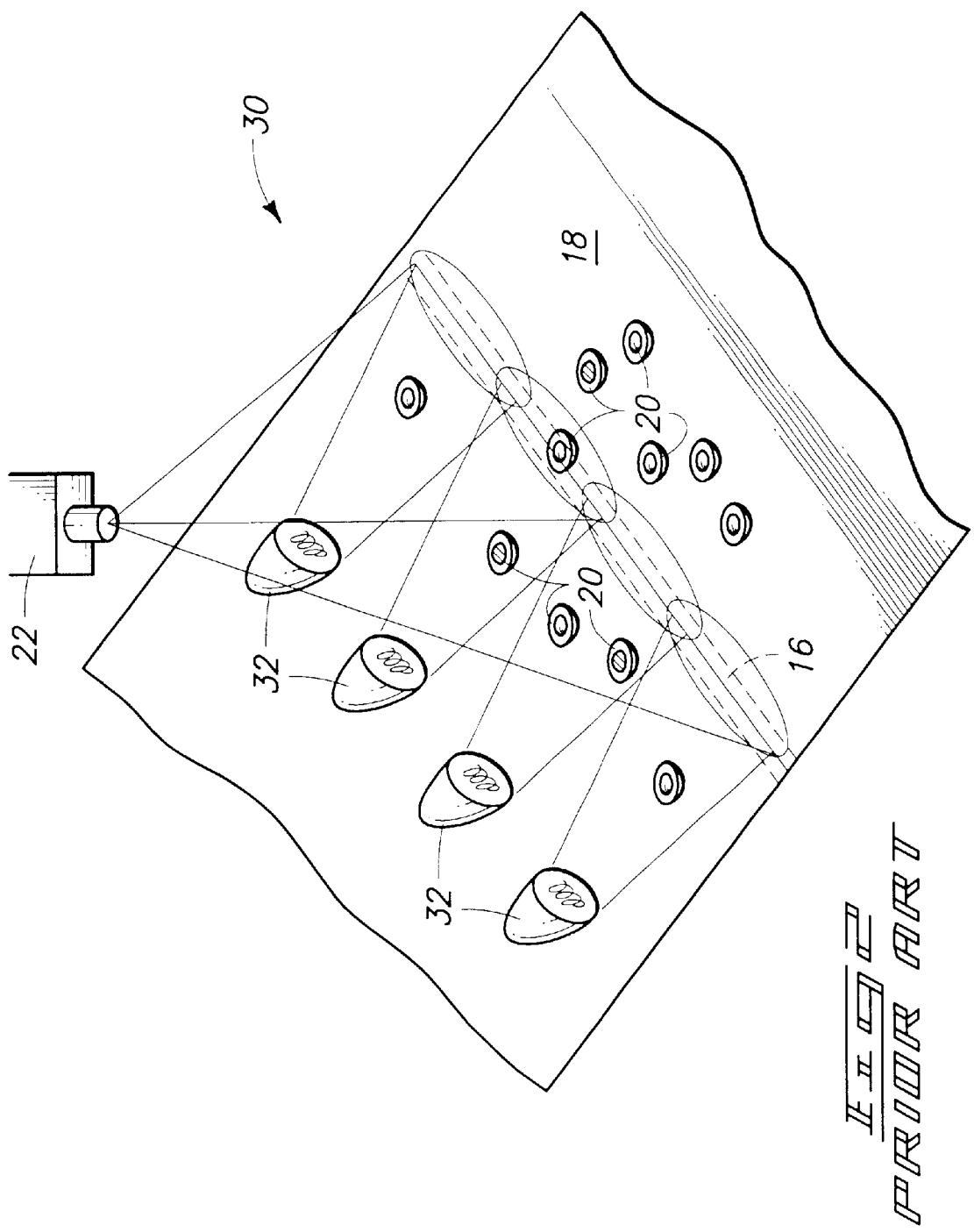
FIG. 2 is an isometric pictorial view of another prior art illumination source showing multiple incandescent light bulbs each having an associated reflector.
Figure 3:
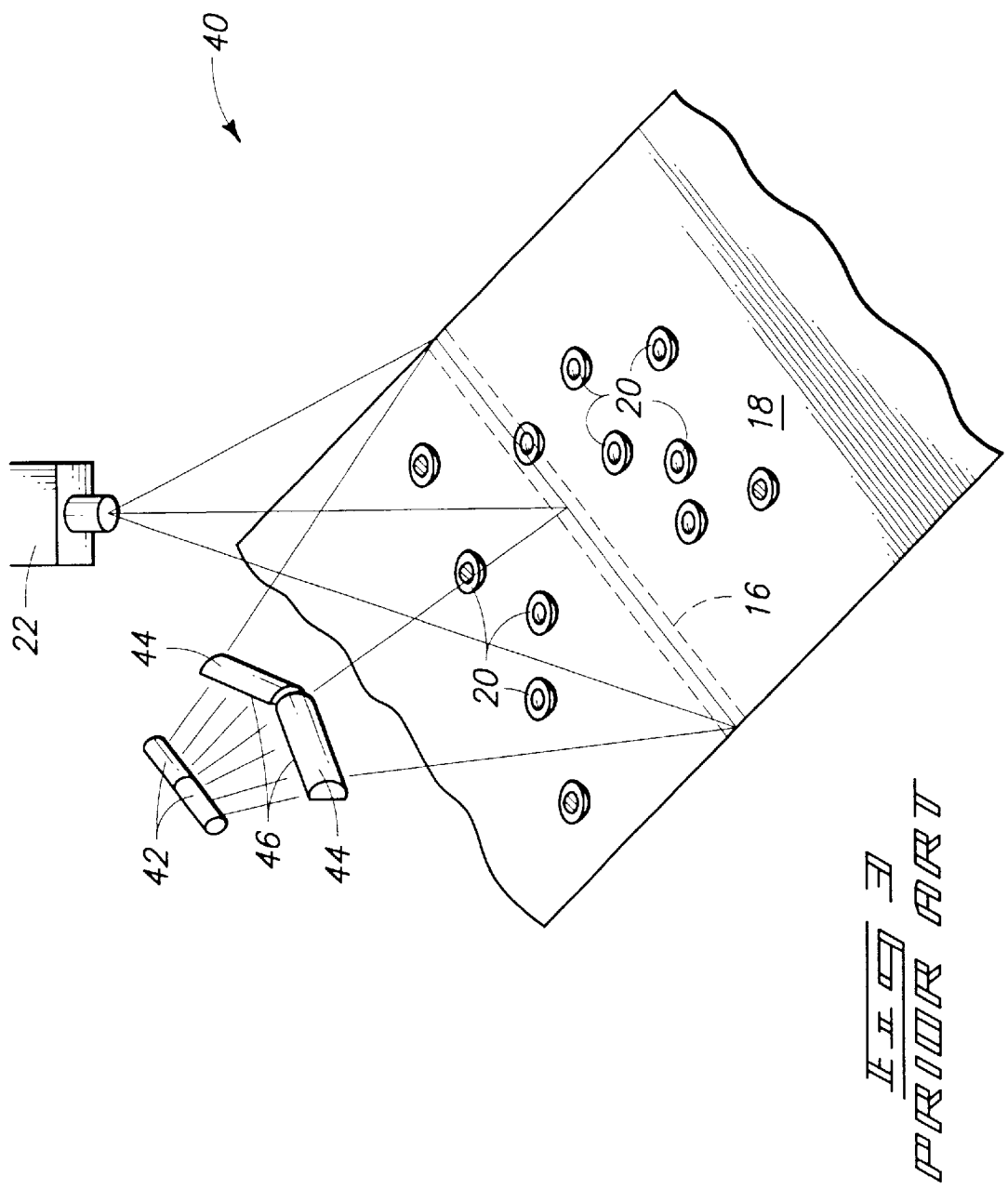
FIG. 3 is an isometric pictorial view of yet another prior art illumination source showing two moderate length HID lamps positioned at the foci of two astigmatic cylindrical lenses.

Illumination sources 90 of FIGS. 8 and 9 provide a stripe of illumination in inspection zone 116 having a substantially uniform intensity across the width of conveyor belt 112. The illumination system includes a pair of illumination sources 90 facing inwardly from opposite sides of inspection zone 116 to provide detector system 118 an unobscured view of inspection zone 116 and to reduce detection errors caused by shadowing. The particular type of HID lamp 92 employed will depend on the specific reflection characteristic under analysis as described with reference to FIGS. 6 and 7. However, Helium lamps preferably employ the prior art reflector structure shown in FIG. 1.

Detector system 118 includes a short wave infrared ("SWIR") camera 140 that is optically co-aligned with a visible camera 142. SWIR camera 140 is manufactured by the assignee of this application using Indium Gallium Arsenide detector arrays available from EG&G Judson of Montgomeryville, Pa., or by Sensors Unlimited of Princeton, N.J. Visible camera 142 is manufactured by the assignee of this application using a silicon detector array available from Thomson CSF of Paris, France. Both cameras are line scanning cameras and therefore have a linear field of view that lies across conveyor belt 112 and defines inspection zone 116. As peaches 114 passes through inspection zone 116, cameras 140 and 142 develop line-by-line video images of peaches 114 that are conveyed to control system 126 for processing.

Visible camera 142 may have 1024 pixels in its detector array whereas SWIR camera 140 may have only 512 pixels in its detector array. Therefore, when cameras 140 and 142 are optically co-aligned, two visible pixels must overlie one SWIR pixel. The two fields of view are co-aligned by means of a cold mirror 144 that reflects the visible portion of the spectrum and transmits the IR portion of the spectrum. Alternatively, if a hot mirror is used, the transmission and reflection paths would be spectrally reversed.

In an alternative embodiment, instead of using two separate cameras and a cold (or hot) mirror, a single camera employing a dichroic beam splitter could be used to combine the visible and IR fields of view. The assignee of this application manufactures such a camera by installing therein a visible and IR dichroic beam splitter in place of a red, green, and blue dichroic beam splitter. This has the added advantage of being a more stable structure. A suitable dichroic beam splitters is available under specification drawing No. SSB-BA005-01 from Canon U.S.A., Inc., located in Irvine, Calif.

FIG. 10 further shows a detailed view of one of peaches 114 in inspection zone 116 in which reflected ray 120 is reflected from peach meat 124, and reflected ray 121 is reflected from peach pit 126 (rays 120 and 121 are actually in a combined field of view, but are shown diverged only for purposes of explanation). When reflected rays 120 and 121 are viewed by cameras 140 and 142, the resulting image signal consists of outputs from two adjacent pixels in visible camera 142 and one pixel in SWIR camera 140.

In an operational example, assume that the video gains of cameras 140 and 142 have been adjusted so that for a reference 100% illumination level reflected from illumination sources 90, both cameras generate a 1-volt signal. Then, with reference to FIG. 5 for Australian peaches, reflected ray 120, from peach meat 124, generates 520 milliVolts ("mV") in visible camera 142 and 520 mV in the SWIR camera 140, while reflected ray 121, from peach pit 126, generates 180 mV in visible camera 142 and 720 mV in the SWIR camera 140.

Subtracting the visible pixel values from the SWIR pixel values yields the following values. For reflected ray 120 (peach meat 124), 520 mV−520 mV=0 mV. Because video levels cannot be negative, any negative values would be set to zero. For reflected ray 121 (peach pits 126), 720 mV−180 mV=540 mV. The net result is that peach meat 124 drops out of the image and only peach pit 126 are detected. This subtraction technique drives the contrast to infinity and makes peach sorting considerably easier. By adjusting the video gain of either the visible or SWIR cameras this effect can be enhanced or diminished.

Another benefit of the subtraction technique is the elimination of "Glint," which is defined as unwanted specular reflection of the light source directly into the field of view of the camera. Fresh peaches 114 are typically wet and, therefore, shiny causing reflection of at least a part of the illumination source directly into the fields of views of cameras 140 and 141. The resulting glint drives both cameras into saturation (1 volt). However, when the visible glint value is subtracted from the SWIR glint value, the result is zero. Therefore, the combined and processed images from cameras 140 and 141 do not include "Glint".

Figure 11:
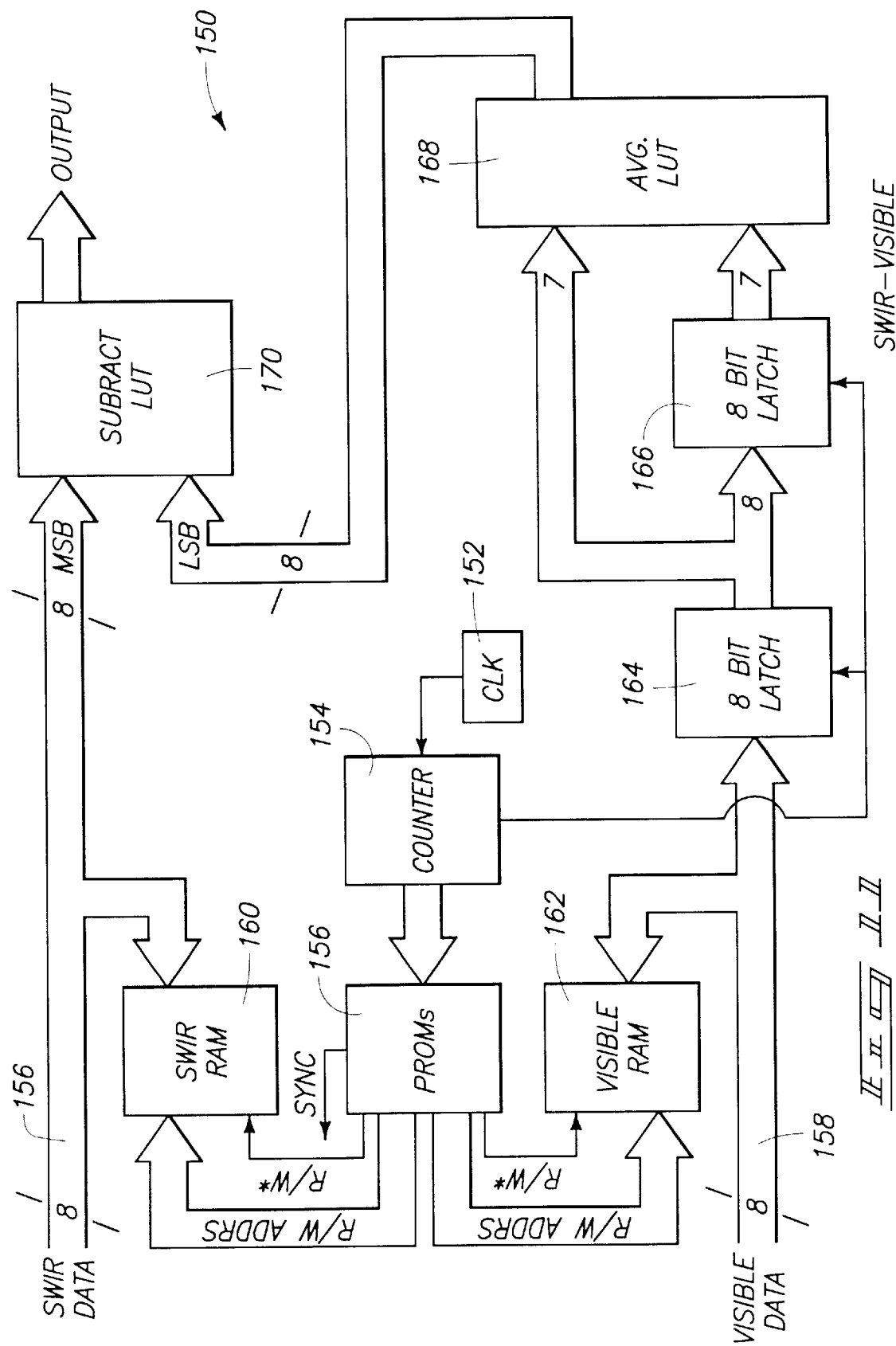
FIG. 11 is a functional block diagram of a technique for subtracting, dividing, or otherwise analyzing visible light values from IR light values in accordance with this invention.

FIG. 11 shows a representative block diagram that may be employed to perform the above-described subtraction or other spectral manipulation, such as division to determine a ratio. Skilled workers will understand that the subtraction or other image processing techniques can be carried out by any computer sufficiently fast to perform the operations in real time. FIG. 11 shows a subtraction processor 150 that carries out the subtraction technique on a pixel by pixel basis in real time without employing a computer.

Subtraction processor 150 is preferably a state machine driven by a clock 152. Clock 152 drives a counter 154, which sequentially provides addresses for a PROM 156. PROM 156 is programmed to provide all the other addresses, read/write not, sync, and latch signals required to operate the remaining circuitry. A sync signal is conveyed to cameras 140 and 142 to each scan of inspection zone 116. The resulting 8-bit data streams from cameras 140 and 142 are conveyed to subtraction processor 150 on an SWIR data bus 156 and a visible data bus 158. The SWIR and visible data is written into sequential locations of respective SWIR and visible RAMs 160 and 162 in response to "write" addresses generated by PROM 156. When the SWIR and visible data for a given scan line is stored, it is accessed and processed before starting the next scan line.

Reading visible data occurs at twice the reading rate of SWIR data because adjacent visible pixels values must be averaged to generate "pseudo visible pixels" that are subtracted from their corresponding SWIR pixel values. This would not be necessary if the SWIR and visible pixel sizes matched.

During an initial data reading operation, data from visible RAM 162 are stored in a first latch 164. During a next reading operation, the data stored in first latch 164 is transferred to a second latch 166 and a next data byte from visible RAM 162 is stored in first latch 164.

The average of A&B is (A+B)/2, which equals (A/2)+(B/2). For a binary coded decimal number, A/2 may be achieved by discarding the least significant bit and shifting one bit to the right. This form of averaging is accomplished by addressing an averaging lookup table ("LUT") 168 with the seven most significant bits from first and second latches 164 and 166. Averaging LUT 168 is programmed to add the two 7-bit addresses together to complete the averaging operation.

The resultant 8-bit average number forms a least significant address byte into a subtraction LUT 170. The corresponding 8-bit SWIR pixel value forms the most significant address byte into subtraction LUT 170. Stored in each memory location of subtraction LUT 170 is the difference between the current SWIR pixel value minus the average visible pixel value. If the difference is negative, zero is stored. Data provided by subtraction LUT 170 is employed by control system 126 to control sorting system 122 such that acceptable peaches are separated from unacceptable peaches.

In the above-described peach pit detecting application, LUT 170 performed the subtraction process. However, other image processing operations, such as addition, division, logs, squares, exponentials, or other functions, could be programmed into LUT 170, or a software-driven equivalent thereof, to enhance the good-to-bad contrast of images. Specific examples are described with reference to FIGS. 12–20.

Because the pixel values being read from RAM 160 are determined by the RAM address, PROM 156 can be programmed to average non-adjacent pixel values. This may be useful if there is some kind of optical non-linearity between cameras 140 and 142. For example, pixel 250 of SWIR camera 140 may not exactly overlay pixels 500 and 501 of visible camera 142, but may instead overlay a small part of pixel 506, all of 507, and most of 508. In this example, pixels 507 and 508 could be averaged and then subtracted from SWIR pixel 250.

Moreover, because SWIR camera 140 employs an InGaAs detector array, and because the technology for making this tertiary material is not well developed, it is difficult to fabricate large InGaAs arrays with flawless pixels. Therefore, most InGaAs detector arrays include some dead pixels. Fortunately, PROM 156 can be programmed to blank out these dead pixels by substituting adjacent good pixel values into the time slots normally allotted to the dead pixels.

Experimental Results

FIGS. 12 to 17 illustrate the imaging performance of an SWIR camera employing a 128 by 128 pixel InGaAs photodetector array while viewing peaches illuminated by different illumination sources. The effects of visible camera 142 and subtraction processor 150 are not shown in FIGS. 12 to 17.

Figure 12:
FIGS. 12 to 17 are photographs representing peach half images and measured sectional reflectance values taken under three sets of experimental conditions to evaluate the IR detection performance of this invention.

FIG. 12 is a Polaroid photograph taken of a television monitor displaying a two-dimensionally image generated from the video output of the SWIR camera viewing a peach with an embedded pit. The illumination source includes an Induim Iodide arc discharge lamp. The peach was prepared by splitting it with a knife and immersing it in a warm 12 percent sodium hydroxide solution for 30 seconds. This preparation removes a portion of the peach flesh tendrils attached to the pit and diminishes chlorophyll effect reflectance from the peach meat. The horizontal white line traversing the peach and pit has been superimposed on the television monitor by a Tektronix waveform measurement system to indicate which displayed scan line is being measured by the waveform measurement system. FIG. 12 clearly shows that the pit is substantially brighter that the surrounding peach flesh.

Figure 13:
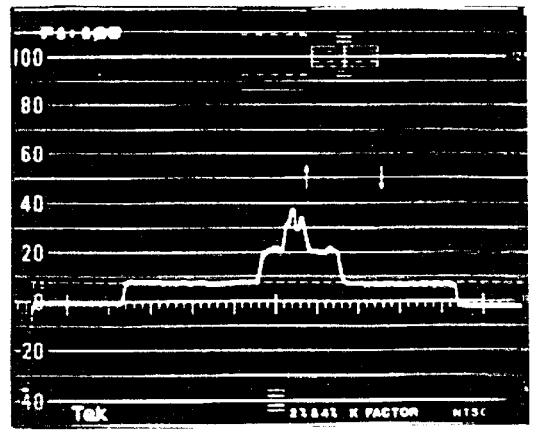

FIG. 13 shows the resulting measurement waveform displayed on the Tektronix waveform measurement system. The centrally located 38 IRE unit waveform blip representing the pit sits atop a 20 IRE unit plateau representing the peach flesh. The black background is at a 7.5 IRE unit level. The pit to meat contrast ranges from about 1.7:1 to 2.4:1.

Figure 14:
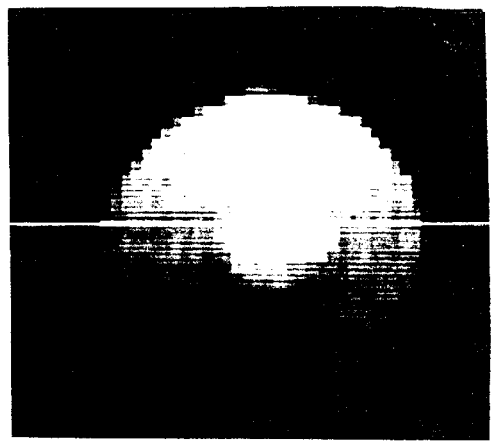
Figure 15:
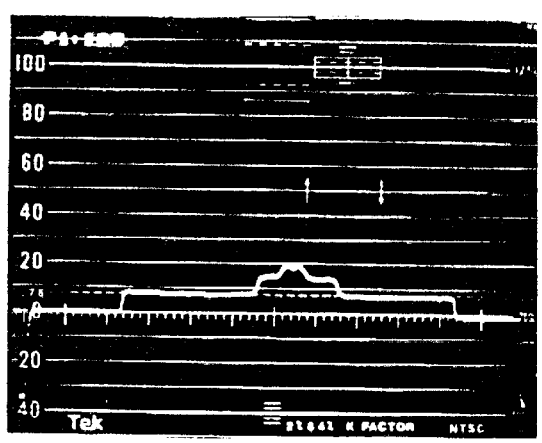

FIGS. 14 and 15 are comparable television and measurement monitor photographs taken with a Helium gas filled low-pressure lamp substituted for the Indium Iodine HID lamp. In this case, the pit reflectance peaks at 20 IRE units and the peach flesh reflectance is at about 15 IRE units. As before, the black background remains at 7.5 IRE units. The contrast ranges from 1.4:1 to 1.66:1.

Figure 16:
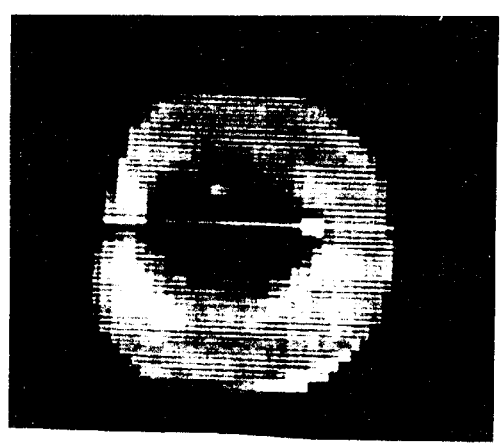
Figure 17:
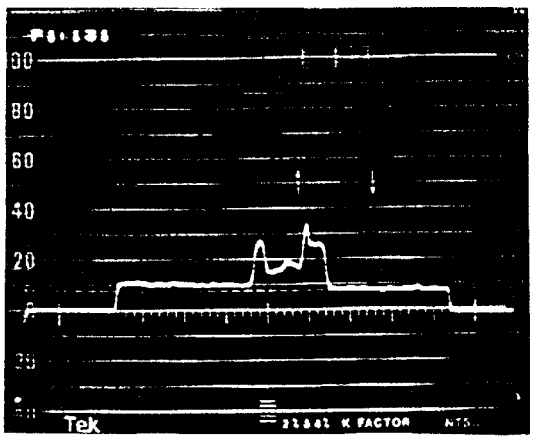

FIGS. 16 and 17 show the small pit fragment detecting ability of the Indium Iodide HID lamp-based system of FIG. 10. These results are particularly dispositive because the fragment is embedded within the pit cavity wall and in the peach flesh, a condition heretofore detected manually. The dark area in the center of the peach half represents the cavity left by the removal of the pit, and the bright spot on the right edge of the cavity represents the pit fragment. In FIG. 17, the sharp rightmost pulse on the oscilloscope trace indicates the location of the pit fragment.

EXAMPLES

In the foregoing experimental results, subtraction can be used to increase the detection contrast because the pit reflectivity is higher than the meat reflectivity in the SWIR wavelengths and lower in the visible wavelengths. Subtraction is not the only image processing technique useful for increasing the detection contrast. For example, image processing employing division (ratio) may improve image contrast for certain illumination and product combinations.

FIGS. 18 and 19, show simplified reflectance versus illumination wavelength graphs for peaches and a generic agricultural product. In particular, illumination is shown by spectral lines representing visible wavelengths 180, SWIR wavelengths 182, and IR wavelengths 184.

In particular, FIG. 18 shows curves representing detected reflectance versus illumination wavelength for peach meat 186 and a peach pit 188. Detected reflectance is shown as milliVolts of detected signal, with peach meat 186 producing a 300 mV signal at visible wavelengths 180 and a 600 mV signal at SWIR wavelengths 182, whereas peach pit 188 produces a 200 mV signal at visible wavelengths 180 and a 900 mV signal at SWIR wavelengths 182.

The conventional, or unaltered, way of determining the contrast is by dividing the highest signal value by the lowest signal value at each wavelength of interest. Accordingly, the unaltered contrast at visible wavelengths 180 is 300 mV/200 mV, which equals 1.5:1 and at SWIR wavelengths 182 is 900 mV/600 mV, which also equals 1.5:1.

Employing subtraction to enhance the contrast entails subtracting the signal values of peach meat 186 and peach pit 188 at visible wavelengths 180 from their signal values at SWIR wavelengths 182, and dividing the resulting values:

For peach meat 186: 600 mV−300 mV=300 mV.

For peach pit 188: 900 mV−200 mV=700 mV.

Contrast=700 mV/300 mV=3.5:1, a 2.33 improvement factor over the unaltered 1.5:1 contrast.

Employing division to enhance the contrast entails dividing the signal values of peach meat 186 and peach pit 188 at visible wavelengths 180 by their signal values at SWIR wavelengths 182, and dividing the resulting values:

For peach meat 186: 600 mV/300 mV=2.0.

For peach pit 188: 900 mV/200 mV=4.5.

Contrast=4.5/2=2.25:1, which is a 1.5 improvement factor over the unaltered 1.5:1 contrast.

FIG. 19 shows an example that more clearly illustrates the usefulness of the division way of enhancing the image contrast. In this case good product 190 produces a 750 mV signal at visible wavelengths 180 and a 200 mV signal at IR wavelengths 184, whereas defect 192 produces a 410 mV signal at visible wavelengths 180 and a 450 mV signal at IR wavelengths 184.

Accordingly, the unaltered contrast at visible wavelengths 180 is 750 mV/410 mV, which equals 1.83:1 and at IR wavelengths 184 is 450 mV/200 mV, which equals 2.25:1.

Employing subtraction to enhance the image contrast (in this case subtracting IR values from visible values):

For good product 190: 750 mV−200 mV=550 mV.

For defect 192: 410 mV−450 mV=−40 mV (set to zero).

Contrast=550 mV/0 mV.

Employing division to enhance the contrast entails dividing the signal values of peach meat 186 and peach pit 188 at visible wavelengths 180 by their signal values at SWIR wavelengths 184, and dividing the resulting values:

For good product 190: 750 mV/200 mV=3.75.

For defect 192: 410 mV/450 mV=0.911.

Contrast=3.75/0.911=4.12:1, which is a 1.83 improvement factor over the best unaltered 2.25:1 contrast.

Examples employing visible, SWIR, and IR wavelengths are described above, although these and other mathematical manipulations are possible in combination with signals generated by detecting multiple (two or more) different portions of a variety of electromagnetic spectra.

Another example illustrates that LUT 170, or its image processing equivalent, can be programmed to enhance the contrast of the image by other image processing methodologies using multiple (two or more) portions of the illumination spectrum. Inage analysis processing techniques are also employed to classify the data into different categories.

Figure 20:
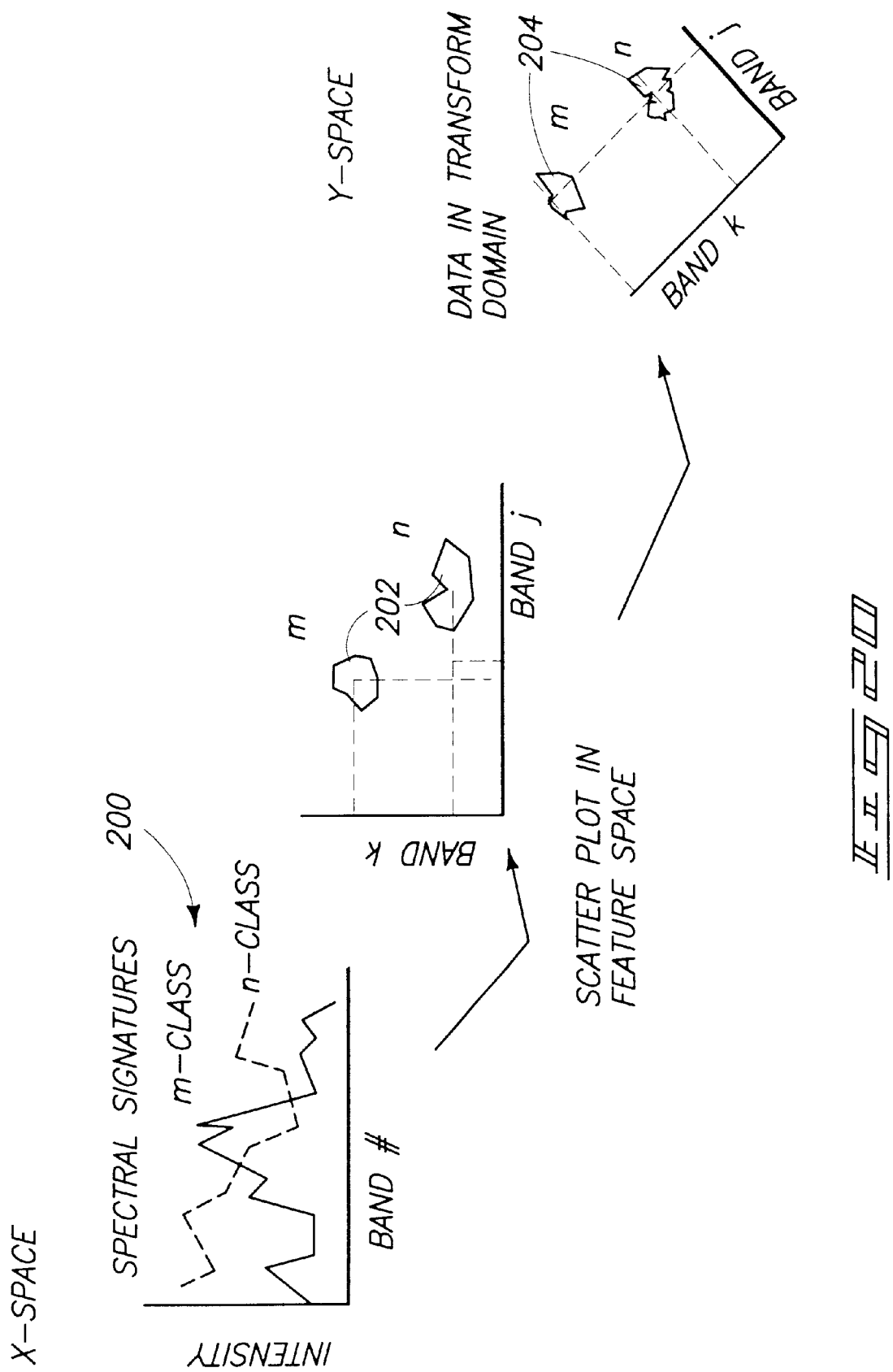
FIG. 20 is a graphical representation of three stages of image processing showing sensed data first processed as spectral data in an X-space, next processed to a scatter plot in a feature space, and finally processed to transform domain data in a Y-space.

FIG. 20 is a graphical representation of three stages of image processing showing sensed data first processed as multiple sets (more than one) of spectral data 200 in an X-space, next processed into scatter plots 202 in a feature space, and finally processed to transform domain data 204 in a Y-space.

For a product being inspected, the sets of spectral data 200 are acquired and formatted into a spectral response image by employing a sorting system, such as peach sorting system 110 of FIG. 10.

The resultant image consists of N by M pixels (N columns and M rows). N=1 when employing a multi-spectral line scanning camera or cameras, such as cameras 140 and 142. In the following mathematical expressions, X represents the vector representation of the spectral response for each pixel in a multi-spectral camera. The dimension of X is n. Therefore, X can be represented by X=[x1, x2, . . . ,xn].

After the spectral image is acquired, the image data are classified into different categories. Classification of vector X into different categories preferably includes performing a feature extraction process and a decision making process.

The feature extracting process employs a subset selector to reduce the dimensionality of X. Mathematical transformations used for selecting subset features that provide increased classification accuracy include:

Ratio (division):

$$y_j = \frac{x_i}{x_k}$$

Log-ratio: $y_j = \log(x_i) - \log(x_k)$

Linear combination: $y_j = a_{j1}x_1 + a_{j2}x_2 + \ldots + a_{jn}x_n$

Principal component transform:

Regression:

$$y_j = a_1 + a_2 \log x_j$$

$$y_j = (a_n x_j)^{\frac{1}{n}}$$

$$y_j = \frac{x_j(\text{Black} + a)}{\text{Black} + x_j}$$

The classifying (decision making) process classifies the feature vector Y into various categories such that the classification error is minimized. Mathematical decision rules for classifying a pixel in an image include:

Calculating the angle between the two vectors that point to the centers of scatter plots 202 in the feature space.

$$\text{Fisher distance} = \frac{D_{kj}}{\sqrt{\zeta_k^2 + \zeta_j^2}};$$

where $\zeta_k^2$ represents the variance of the kth feature vector component.

City block distance $= D_{kj} = |y_k - m_k| + |y_j - m_j| + \ldots$;

for k=1, 2, . . . , and j=1, 2, . . . ; where:

$$m_k = \frac{\sum_{k=1}^{k=N_t} y_k}{N_t}$$

and Nt is the number of training samples. Each pixel is classified by calculating the minimum of $D_{kj}$.

$$\text{Direction cosines} = \cos\theta = \frac{(Y, M)}{\|Y\|\|M\|}; \text{ where}$$

$$\|Y\| = \sqrt{y_k^2 + y_j^2 + \ldots}$$

Euclidean distance $D_{kj} = \sqrt{(y_{k-m_k})^2 + (y_{j-m_j}) + \ldots}$;

for k=1, 2, . . . ; and j=1, 2, . . . ; where j≠k.

Definitions:

$x_k$=pixel value of band k at position (m,n)

$m_k$=the mean of band k $\zeta_k^2$=the variance of band k

Classifying may also be based on image shape information.

It will be obvious to those having skill in the art that many changes may be made to the details of the above-described embodiment of this invention without departing from the underlying principles thereof. Accordingly, it will be appreciated that this invention is also applicable to article inspection and detection applications other than those found in peach inspection applications. The scope of the present invention should, therefore, be determined only by the following claims.

What is claimed is:

1. A method of sorting articles that are moved past an inspection zone, comprising:

illuminating the articles in the inspection zone with visible and infrared radiation;

sensing the visible and infrared radiation reflected from the articles in the inspection zone and generating visible and infrared image data;

extracting feature data from the visible image data and assigning a first numerical value representing a feature of a discrete area from respective articles;

extracting feature data from the infrared image data and assigning a second numerical value representing the feature of the discrete area of the respective articles;

subtracting the first numerical value from the second numerical value to obtain a contrast value;

rejecting the contrast value if less than a threshold value;

classifying the contrast value into a class category if the contrast value is not less than the threshold value; and separating the articles into acceptable articles and unacceptable articles in response to the class category.

2. The method of claim 1 in which the acceptable articles include peaches, and the unacceptable articles include at least one of peach pits and pit fragments.

3. The method of claim 1 in which the illuminating includes providing an Indium Iodide high-intensity discharge lamp or a Helium plasma discharge lamp.

4. The method of claim 1 in which the sensing includes sensing the visible and infrared radiation with a wavelength-selective camera system.

5. The method of claim 1 in which the extracting and classifying are carried out by at least one of a lookup table and a computer program.

6. The method of claim 1 in which extracting the feature data further includes calculating a statistical distance between clusters of the feature data.

7. The method of claim 1 in which extracting the feature data further includes calculating at least one of a value, a mean, a variance, and a shape of clusters of the feature data.

8. An article sorting system that conveys the articles on a conveyor belt and past an inspection zone, comprising:

an illumination system emitting visible and infrared radiation for illuminating the articles in the inspection zone;

a detector system for sensing the visible and infrared radiation reflected from the articles in the inspection zone and generating visible and infrared image data;

a processor extracting feature data from the visible image data and assigning a first numerical value representing a feature of a discrete area from respective articles and extracting feature data from the infrared image data and assigning a second numerical value representing the feature of the discrete area of the respective articles, and then subtracting the first numerical value from the second numerical value to obtain a contrast value, the processor rejecting the contrast value if less than a threshold value and classifying the contrast value into a class category if the contrast value is not less than the threshold value; and a sorter responsive to the class category for separating the articles into acceptable articles and unacceptable articles.

9. The system of claim 8 in which the acceptable articles include peaches, and the unacceptable articles include at least one of peach pits and pit fragments.

10. The system of claim 8 in which the illumination system includes at least one high-intensity discharge lamp that emits the visible and infrared radiation to illuminate the inspection zone.

11. The system of claim 8 in which the detector system senses the visible and infrared radiation with a wavelength-selective beam splitter-based camera or a beam splitter and two cameras.

12. The system of claim 8 in which the detector system senses the visible radiation with at least one line scanning wavelength-selective detector array-based camera.

13. The system of claim 8 in which the processor employs a lookup table for processing the difference between the visible image data and the infrared image data.

* * * * *

UNITED STATES PATENT AND TRADEMARK OFFICE
CERTIFICATE OF CORRECTION

PATENT NO.    : 6,410,872 B2
DATED         : June 25, 2002
INVENTOR(S)   : Duncan Campbell et al.

It is certified that error appears in the above-identified patent and that said Letters Patent is hereby corrected as shown below:

Column 7,
Line 16, replace "control system 126" with -- control system 127 --.

Column 9,
Line 42, replace "control system 126" with -- control system 127 --.

Column 12,
Line 1, replace "Inage" with -- Image --.

Line 38, replace " $y_j = a_j x_1 + a_j x_2 + \bullet \bullet \bullet + a_{jn} x_n$ " with -- $y_j = a_{j1} x_1 + a_{j2} x_2 + \bullet \bullet \bullet = a_{jn} x_n$ --.

Column 13,
Line 17, replace " $\sqrt{(y_{k-m_k})^2 + (y_j - m_j) + \ldots}$ ;" with -- $\sqrt{(y_k - m_k)^2 + (y_j - m_j)^2 + \bullet \bullet \bullet}$ ; --.

Signed and Sealed this

Twenty-second Day of July, 2003

JAMES E. ROGAN
*Director of the United States Patent and Trademark Office*